United States Patent [19]
Powell et al.

[11] Patent Number: 5,976,783
[45] Date of Patent: Nov. 2, 1999

[54] BIS-MALEIMIDO CROSS-LINKING AGENTS

[75] Inventors: Michael J. Powell, Danville, Calif.;
Lutz F. Tietze, Gottingen, Germany

[73] Assignee: Boehringer Mannheim Corporation, Indianapolis, Ind.

[21] Appl. No.: 08/883,632

[22] Filed: Jun. 26, 1997

Related U.S. Application Data

[63] Continuation of application No. 08/592,015, Jan. 26, 1996, abandoned.

[51] Int. Cl.$^6$ .............................................. C07D 207/333
[52] U.S. Cl. ............................ 435/4; 435/183; 548/413; 548/520; 548/521; 558/11
[58] Field of Search .................................. 548/520, 521, 548/413; 558/11; 435/183, 4

[56] References Cited

U.S. PATENT DOCUMENTS

| | | | |
|---|---|---|---|
| 4,179,337 | 12/1979 | Davis et al. | 435/181 |
| 4,493,795 | 1/1985 | Nestor, Jr. et al. | 260/112.5 E |
| 4,671,958 | 6/1987 | Rodwell et al. | 424/85 |
| 4,708,929 | 11/1987 | Henderson | 435/7 |
| 4,766,106 | 8/1988 | Katre et al. | 514/12 |
| 5,011,910 | 4/1991 | Marshall et al. | 530/329 |
| 5,149,783 | 9/1992 | Sommergruber et al. | 530/326 |
| 5,164,300 | 11/1992 | Marshall et al. | 435/23 |
| 5,166,322 | 11/1992 | Shaw et al. | 530/351 |
| 5,171,662 | 12/1992 | Sharma | 435/5 |
| 5,362,625 | 11/1994 | Krevolin et al. | 435/7.6 |
| 5,412,083 | 5/1995 | Giese et al. | 536/20 |
| 5,434,052 | 7/1995 | Khanna | 435/7.6 |
| 5,506,115 | 4/1996 | Toth et al. | 435/7.6 |

FOREIGN PATENT DOCUMENTS

| | | |
|---|---|---|
| 0314127 | 5/1989 | European Pat. Off. |
| 0419081 | 3/1991 | European Pat. Off. |
| 0530998 | 3/1993 | European Pat. Off. |
| 0618192 | 10/1994 | European Pat. Off. |
| 2276621 | 10/1994 | United Kingdom |
| WO 96/34976 | 11/1976 | WIPO |
| WO 86/02666 | 5/1986 | WIPO |
| WO 90/05749 | 5/1990 | WIPO |
| WO 92/03559 | 3/1992 | WIPO |
| WO 95/16894 | 6/1995 | WIPO |
| WO 96/12492 | 5/1996 | WIPO |
| WO 97/08194 | 3/1997 | WIPO |

OTHER PUBLICATIONS

Chen et al., "A chimera antibody erythroimmunoassay for detecting HBsAg in human sera" *Res. Virol.* (1990) 141:337–342.

Zabin, "β-galactosidase α complementation" *Mol. Cell. Biochem.* (1982) 49:87–96.

Welply et al., "β-galactosidase ω-complementation with a small cyanogen bromide peptide" *Biochem. Biophys. Res. Comm.* (1980) 93(1):223–227.

Henderson, "CEDIA™, a new homogeneous immunoassay system" *Clin. Chem.* (1986) 32:1637–1641.

Coty, "CEDIA® homogeneous immunoassays: Current status and future prospects" *J. Clin. Immunoassay* (1994) 17:144–150.

Fernandez–Lafuenta et al., "Stabilization of soluble proteins by intramolecular crosslinking with polyfunctional micromolecules, poly–(glutaraldehyde–like) structure; beta-galactosidase, penicillin–amidase, trypsin and chymotrypsin immobilization and enzyme stabilization" *Stud. Org. Chem.* (1993) 47:315–322.

Wong, "Chemistry of protein conjugation and cross–linking" (1991) CRC Press Inc., Boca Raton. The title page and table of contents only are included herewith.

Kramer et al., "HTLV–III gag protein is processed in yeast cells by the virus pol–protease" *Science* (1986) 231:1580–1584.

Kohl et al., "Active human immunodeficiency virus protease is required for viral infectivity" *Proc. Natl. Acad. Sci* (1988) 85:4686–4690.

Kräusslich et al., "Activity of purified biosynthetic proteinase of human immunodeficiency virus on natural substrates and synthetic peptides" *Proc. Natl. Acad. Sci.* (1989) 86:807–811.

Baum et al., "β–galactosidase containing a human immunodeficiency virus protease cleavage site is cleaved and inactivated by human immunodeficiency virus protease" *Proc. Natl. Acad. Sci.* (1990) 87:10023–10027.

(List continued on next page.)

*Primary Examiner*—Joseph K. McKane
*Attorney, Agent, or Firm*—Morrison&Foerster LLP

[57] ABSTRACT

Formation of an intramolecular cross-link in enzyme donor polypeptide fragments of β-galactosidase, thereby forming a cyclic enzyme donor which is hindered from complementation with an enzyme acceptor fragment to form active of β-galactosidase. The cyclic enzyme donor can be linearized by cleaving to restore complementation ability. Assays in which such cyclic enzyme donors are linearized by specific analytes are disclosed, as well as novel homobifunctional bis-maleimido cross-linking agents of the formula

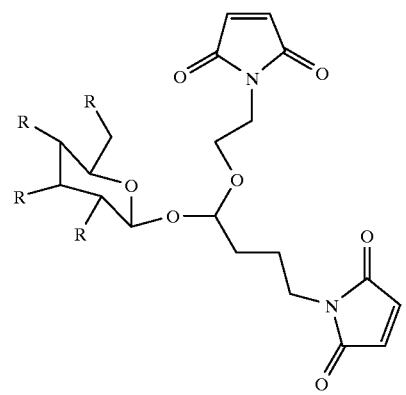

wherein R is hydroxy or acetate.

18 Claims, 2 Drawing Sheets

OTHER PUBLICATIONS

Liebig et al., "Proteinase trapping: Screening for viral proteinase mutants by α complementation" *Proc. Natl. Acad. Sci.* (1991) 88:5979–5983.

Thornberry et al., "A novel heterodimeric cysteine protease is required for interleukin-1β processing in monocytes" *Nature* (1992) 356:768–774.

Enari et al., "Involvement of an ICE–like protease in Fas–mediated apoptosis" *Nature* (1995) 375:78–81.

Srinivasachar et al., "New protein cross–linking reagents that are cleaved by mild acid" *Biochem.* (1989) 28:2501–2509.

Partis et al., "Cross–linking of protein by ω–maleimido alkanoyl N–hydroxysuccinimido esters" *J. Prot. Chem.* (1983) 2:263–277.

Casadaban et al., "β–galactosidase gene fusions for analyzing gene expression in *Escherichia coli* and yeast" *Meth. Enzymol.* (1983) 100:293–308.

Meissner et al., "Bacteriophage λ cloning system for the construction of directional cDNA libraries" *Proc. Natl. Acad. Sci.* (1987) 84:4171–4175.

Ghosh et al., "The development of cyclic sulfolanes a novel and high–affinity $P_2$ ligands for HIV–1 protease inhibitors" *J. Med. Chem.* (1994) 37:1177–1188.

Ghosh et al., "Structure–based design of HIV–1 protease inhibitors: Replacement of two amides and a 10π–aromatic system by a fused bis–tetrahydrofuran" *J. Med. Chem.* (1994) 37:2506–2508.

Khanna et al., "A new homogeneous enzyme immunoassay using recombinant enzyme fragments" Clin.Chim. Acta (1989) 185:231–239.

Khanna et al., "EBV peptide epitope sensitization restores human cytotoxic T cell recognition of Burkitts's lymphoma cells" *J. Immunol.* (1993) 150:5154–5162.

Büttner et al., "Screening of inhibitors of HIV–1 protease using an *Escherichia coli* cell assay" *Biochem. and Biophys. Res. Commun.* (1997) 233:36–38.

Fournout et al., "Development and standardization of an immuno–quantified solid phase assay for HIV–1 aspartyl protease activity and its application to the evaluation of inhibitors" *Anal. Biochem.* (1997) 69:1746–1752.

Johnson et al., "Heterobifunctional cross–linkers containg 4,9–Dioxa–1,12–dodecanediamine spacers" *Bioconjugate Chem.* (1997) 8:447–452.

Jolley, "Fluorescence polarization assays for the detection of protease and their inhibitors" *J. Biomed. Screen.* (1996) 1(1):33–38.

Levine et al., Measurement of specific protease activity utilizing fluorescent polarization *Anal. Biochem.* (1997) 247:83–88.

Dissertation by Karsten Machholz, University of Göttingen, copyright by Cuvillier Verlag in 1995, accompanied by English translation of excerpts of the dissertation, prepared by Boehringer Mannheim Corporation, Indianapolis.

Jörnvall, H, et al., "Probe of β–galactosidase structure with iodoacetate. Differential reactivity of thiol groups in wild–type and mutant forms of β–galactosidase" *Biochemistry* (1978) 17(24):5160–5164.

Langley et al., "β–galactosidase α complementation: Properties of the complemented enzyme and mechanism of the complementation reaction" *Biochemistry* (1976) 15(22):4866–4875.

Westby, M., et al., "Preparation and characterization of recombinant proricin containing an alternative protease–sensitive linker sequence" *Bioconjugate Chem.* (1992) 3:375–381.

Windheuser, M.G., et al., "Expression of functional beta–galatosidase containing to coxsackievirus 3C protease as an internal fusion" *Biochem. Biophys. Res. Comm.* (1991) 177(1):243–251.

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 8 amino acids
      (B) TYPE: amino acid
      (C) STRANDEDNESS: single
      (D) TOPOLOGY: linear (xi) SEQUENCE DESCRIPTION: SEQ ID NO:1:

Ser Gln Asn Tyr Pro Ile Val Gln
1             5

(2) INFORMATION FOR SEQ ID NO:2:

(i) SEQUENCE CHARACTERISTICS:
      (A) LENGTH: 10 amino acids
      (B) TYPE: amino acid
      (C) STRANDEDNESS: single (D) TOPOLOGY: linear (xi) SEQUENCE DESCRIPTION: SEQ ID NO:2:

Val Ser Phe Asn Phe Pro Gln Ile Thr Leu
1               5                   10

(2) INFORMATION FOR SEQ ID NO:3:

(i) SEQUENCE CHARACTERISTICS:
            (A) LENGTH: 5 amino acids
            (B) TYPE: amino acid
            (C) STRANDEDNESS: single
            (D) TOPOLOGY: linear (xi) SEQUENCE DESCRIPTION: SEQ ID NO:3:

Xaa Val Xaa Asp Xaa
1               5

(2) INFORMATION FOR SEQ ID NO:4:

(i) SEQUENCE CHARACTERISTICS:
            (A) LENGTH: 4 amino acids
            (B) TYPE: amino acid
            (C) STRANDEDNESS: single
            (D) TOPOLOGY: linear (ix) FEATURE:
            (A) NAME/KEY: Modified-site
            (B) LOCATION: 4
            (D) OTHER INFORMATION: /product= "OTHER"
                /label= Asp-NH-CH3
                /note= "N-methyl aspartic acid"

(ix) FEATURE:
            (A) NAME/KEY: Modified-site
            (B) LOCATION: 1
            (D) OTHER INFORMATION: /product= "OTHER"
                /label= Ac-Tyr
                /note= "Acetyl tyrosine"

(xi) SEQUENCE DESCRIPTION: SEQ ID NO:4:

Tyr Val Ala Asp
1

(2) INFORMATION FOR SEQ ID NO:5:

(i) SEQUENCE CHARACTERISTICS:
            (A) LENGTH: 4 amino acids
            (B) TYPE: amino acid
            (C) STRANDEDNESS: single
            (D) TOPOLOGY: linear (ix) FEATURE:
            (A) NAME/KEY: Modified-site
            (B) LOCATION: 4
            (D) OTHER INFORMATION: /note= "chloromethylketone group
                attached"

(ix) FEATURE:
            (A) NAME/KEY: Modified-site
            (B) LOCATION: 1
            (D) OTHER INFORMATION: /product= "OTHER"
                /label= Ac-Tyr
                /note= "Acetyl tyrosine"

(xi) SEQUENCE DESCRIPTION: SEQ ID NO:5:

Tyr Val Ala Asp
1

(2) INFORMATION FOR SEQ ID NO:6:

(i) SEQUENCE CHARACTERISTICS:

-continued (A) LENGTH: 54 base pairs
(B) TYPE: nucleic acid
(C) STRANDEDNESS: single
(D) TOPOLOGY: linear (xi) SEQUENCE DESCRIPTION: SEQ ID NO:6:

GATACGAATT CTCAGAACTA TCCGATCGTT CAGTCACTGG CCGTCGTTTT ACAA    54

(2) INFORMATION FOR SEQ ID NO:7:

(i) SEQUENCE CHARACTERISTICS:
      (A) LENGTH: 60 base pairs
      (B) TYPE: nucleic acid
      (C) STRANDEDNESS: single
      (D) TOPOLOGY: linear (xi) SEQUENCE DESCRIPTION: SEQ ID NO:7:

GATACGAATT CTGTAAGCTT TAACTTTCCG CAGATCACCC TGCTGGCCGT CGTTTTACAA    60

(2) INFORMATION FOR SEQ ID NO:8:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (xi) SEQUENCE DESCRIPTION: SEQ ID NO:8:

CTGGCTTAAC TATGCGGCAT C    21

(2) INFORMATION FOR SEQ ID NO:9:

(i) SEQUENCE CHARACTERISTICS:
      (A) LENGTH: 4 amino acids
      (B) TYPE: amino acid
      (C) STRANDEDNESS: single
      (D) TOPOLOGY: linear (xi) SEQUENCE DESCRIPTION: SEQ ID NO:9:

Gly Gly Gly Cys

BIS-MALEIMIDO CROSS-LINKING AGENTS

Reference to related applications

This application is a file wrapper continuation of application Ser. No. 08/592,015, filed Jan. 26, 1996, now abandoned.

BACKGROUND OF THE INVENTION

This invention relates to compounds, compositions and methods useful for the detection of analytes by complementation of polypeptide fragments of β-galactosidase. Specifically, the invention relates to cross-linking agents, formation of an intramolecular cross-link in enzyme donor polypeptides of β-galactosidase, and the use of such compositions in the detection and quantitation of analytes in samples.

In the past, various synthetic and natural antigenic polypeptides and polypeptide fragments have been conjugated to high molecular weight protein carriers such as latex functionalized SEPHAROSE (Pharmacia, Inc.), tetanus toxoid, keyhole limpet hemocyanin, agarose and cellulose to detectable labels such as fluorophores, and to chemotherapeutic agents using bifunctional cross-linking agents. U.S. Pat. No. 4,493,795 and PCT publication WO 90/05749 (published May 31, 1990) are exemplary. Such cross-linking agents have also been used to attach bioactive or cytotoxic agents, dyes, radioactive compounds and the like to antibody molecules. U.S. Pat. No. 4,671,958 is exemplary. Antibodies have been linked together using such agents. See Chen, *Res. Virol.* 141:337–42 (1990). Cross-linking agents have also found use for modifying bioactive and therapeutically useful polypeptides by conjugation with polymers such as polyethylene glycol to enhance pharmacokinetic properties. U.S. Pat. Nos. 5,166,322, 4,179,337 and 4,766,106 are exemplary.

β-Galactosidase is a tetrameric protein with a monomer molecular weight of approximately 116,000 Daltons. The monomer is composed of 1023 amino acids. Intracistronic complementation is the known phenomenon whereby individually inactive peptide fragments of the enzyme spontaneously associate to form an active β-galactosidase protein. Among the first β-galactosidase complementation pairs investigated in depth was the M15/CNBr2 system described by Langley and Zabin, *Biochemistry* 15:4866 (1976). M15 is a deletion mutant of β-galactosidase lacking amino acids 11–41. The CNBr2 peptide consists of amino acids 3–92 of β-galactosidase and is prepared from cyanogen bromide cleavage of the intact enzyme. When M15 and CNBr2, which are individually inactive, are incubated together under appropriate conditions, the two peptides complement or associate with eachother to form fully active, tetrameric β-galactosidase. In this system, CNBr2, the N-terminal peptide, is referred to as the α-enzyme donor. M15, which has the N-terminal deletion, is referred to as the α-enzyme acceptor. The general phenomenon which uses the reassociation of the domains of β-galactosidase to form active β-galactosidase from inactive fragments is referred to as complementation. Other combinations of α-enzyme donors and α-enzyme acceptors have been described. See Zabin, *Mol. and Cellular Biochem* 49:84 (1982). Each is a variant derived from the natural β-galactosidase sequence.

Complementation of a C-terminal peptide and corresponding C-terminal deletion protein has also been described. An example of this phenomenon, known as omega-complementation, is X-90, a β-galactosidase deletion variant lacking 10 amino acids at the C-terminus and CNBr24, a peptide comprising amino acids 990–1021 of β-galactosidase. As in the case of α-complementation, ω-enzyme donor polypeptides and ω-enzyme acceptor proteins are inactive but reassociate to form enzymatically active tetramer. See Welphy, *Biochem. Biophys. Res. Comm.* 93:223 (1980).

β-Galactosidase complementation activity has been exploited to produce sensitive quantitative assays for both high and low molecular weight analytes. U.S. Pat. Nos. 5,362,625 and 4,708,929 disclose, inter alia, a variety of enzyme donor and enzyme acceptor polypeptide compositions for use in antibody and receptor binding assays. The enzyme donors and enzyme acceptors are generated by means of recombinant DNA or polypeptide synthesis techniques familiar to skilled artisans.

These approaches allow great flexibility and control over the design of enzyme donor and enzyme acceptor molecules. The use of genetic engineering techniques allows the sequence and length of the enzyme donor and enzyme acceptor polypeptides to be modified to maximize assay performance and reagent stability. Enzyme donors optimized for chemical coupling to analyte and enzyme donors genetically fused to analyte peptides or proteins have been described, and immunoassays using these compositions are commercially available. See Henderson, *Clin. Chem.* 32:1637 (1986); Khanna, *Amer. Clin. Lab* 8:14 (1989) and Coty, *J. Clin. Immunoassay* 17:144 (1994).

One problem not addressed by the art in this area involves the reduction of background interference in these complementation assays. Because the enzyme donor and enzyme acceptor molecules spontaneously combine to form active enzyme, antibody or receptor binding to the unmodified enzyme donor or enzyme acceptor fragments has been relied upon in the past to inhibit such undesirable complementation. This approach has not fully succeeded.

SUMMARY OF THE INVENTION

This invention provides materials and methods for complementation assays using enzyme donor polypeptides that have been intramolecularly cross-linked. By "enzyme donor" or "enzyme donor polypeptide," we mean an enzymatically inactive polypeptide fragment of β-galactosidase comprising a peptide sequence capable of combining or associating with an enzyme acceptor to form active β-galactosidase enzyme. By "enzyme acceptor" or "enzyme acceptor polypeptide," we mean an enzymatically inactive polypeptide fragment of β-galactosidase produced by a deletion mutant of the β-galactosidase gene which, when combined or associated with an enzyme donor, is capable of forming active β-galactosidase enzyme by the process of complementation. These assays employing intramolecularly cross-linked enzyme donors are based on the observation made by the current inventors that complementation between an enzyme donor polypeptide and an enzyme acceptor can be greatly reduced or inhibited by the introduction of an intramolecular cross-link into the enzyme donor polypeptide. By "cross-link" or "intramolecular cross-link," we mean the covalent chemical attachment of a cross-linking agent between two reactive amino acid residues in an enzyme donor polypeptide, thereby giving the polypeptide a cyclic structure. Such cross-linked enzyme donors are also referred to herein as "cyclic enzyme donors."

It has also been observed that full complementation activity can be regained by breaking or cleaving the cyclic polypeptide, thereby linearizing the polypeptide. This phenomenon is useful in an assay format where the intramolecularly cross-linked donor peptide, or cyclic peptide, can be linearized by the action of, or because of, the presence of a specific analyte. A significant advantage of this system over those previously described is the extremely low inherent background signal. Genetic engineering techniques can be employed to position the points of the enzyme donor cross-linking so that complementation activity of the cross-linked molecules is minimized. While not intending to be bound by theory, we speculate that the cross-linked enzyme donor peptide is sterically hindered from assuming a conformation that allows association with the enzyme acceptor peptide to form active enzyme.

A peptide is any compound formed by the linkage of two or more amino acids by amide (peptide) bonds, usually a polymer of α-amino acids in which the α-amino group of each amino acid residue (except the $NH_2$-terminal) is linked to the α-carboxyl group of the next residue in a linear chain. The terms peptide, polypeptide and poly(amino acid) are used synonymously herein to refer to this class of compounds without restriction as to size. The largest members of this class are referred to as proteins.

A complex is a reversible association of chemical compounds or moieties held together by weak bonds or other forces, such as an enzyme-substrate complex (an association of an enzyme and one or more substrates that is the reacting moiety in an enzyme-catalyzed reaction), an antigen-antibody complex, a hapten-antibody complex, or an active enzyme complex of β-galactosidase formed by complementation of an enzyme donor and an enzyme acceptor.

Other aspects of the present invention include methods for making the cross-linked enzyme donor polypeptides, novel homobifunctional bis-maleimido cross-linking agents and assay methods which employ cross-linked enzyme donor polypeptides.

Other aspects and advantages of the present invention will be apparent upon consideration of the following detailed description of the invention, including illustrative examples of the practice thereof.

BRIEF DESCRIPTION OF THE DRAWINGS

The present invention will be better understood by reference to the following detailed description of the invention when considered in combination with the drawings that form part of the specification, wherein.

DETAILED DESCRIPTION OF THE INVENTION

Figure 1:
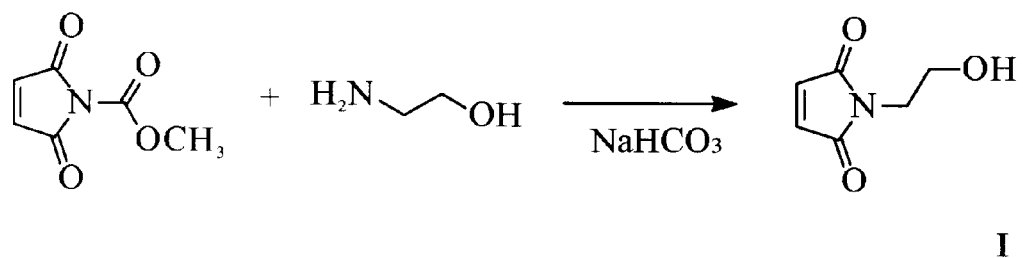
FIG. 1 illustrates a particular synthetic scheme for preparing N-(2-trimethylsiloxyethyl)maleimide.

This invention first provides cross-linked enzyme donor polypeptide sequences of β-galactosidase. Cross-linked β-galactosidase enzyme donor polypeptides of the invention encompass β-galactosidase sequences that contain reactive amino acid residues that permit attachment of a cross-linking agent which comprises cross-linking moieties. Reactive amino acid residues permitting attachment to such moieties are α- or ε- amino groups (e.g., lysine), α-, β- or γ-carboxyl groups (e.g., aspartic acid or glutamic acid), thiol groups (e.g., cysteine), and aromatic rings (e.g., histidine or tyrosine). The cross-linking moiety is an integral part of the cross-linking agent and comprises a chemical moiety or functional group that enables the cross-linking agent to covalently bond to reactive amino acid residues. For example, a cross-linking agent useful to covalently couple thiol groups of proteins and peptides is bis-maleimidohexane (BMH). This cross-linking agent comprises a hexamethylene moiety having maleimido cross-linking moieties attached to each end of the hexamethylene. Other exemplary cross-linking agents are described in *Chemistry of Protein Conjugation and Cross-Linking*, S. S. Wong, CRC Press, 1993.

The amine groups of reactive amino acids in the enzyme donor polypeptide may be cross-linked by reaction with an amino group-reactive moiety of the cross-linking agent. N-hydroxysuccinimide, dimethylsuberimidate, phenyldiisocyanate, phenyldiisothiocyanate, difluorodinitrobenzene and cyanic chloride are exemplary cross-linking agents.

The thiol groups of reactive amino acids may be cross-linked by reaction with a sulfhydryl-reactive moiety of the cross-linking agent. Exemplary are S-pyridyl, maleimide and bromoacetyl moieties.

The carboxyl groups of reactive amino acids may be cross-linked by reaction with carbodiimide or hydrazide moieties.

The cross-linking moieties may be homo- or heterobifunctional such that cross-linking between the appropriate residues, preferably at or near the N-terminal and C-terminal residues of the enzyme donor, is accomplished. Thus, the cross-linking agent will have two reactive groups capable of covalent chemical attachment to the amino, thiol, carboxyl or aromatic groups of the desired amino acid residues of the enzyme donor polypeptide.

The enzyme donor may comprise an inserted cassette or recognition site, the nature of which depends upon the application to which the cross-linked enzyme donor polypeptides will be put. The recognition site may comprise a peptide sequence or a nucleic acid sequence that is cleavable by an enzyme or a specific protease, nuclease or endoglycosidase by virtue of containing a protease, nuclease or glycosidase recognition sequence. Alternatively, the recognition site may comprise a substrate recognition site for a specific hydrolase enzyme such as a phosphatase, glycosidase, amidase or esterase. Viral proteases such as HIV-1 and HIV-2 protease, coxsackie virus protease and herpes virus protease recognize specific peptide substrate sequences of the host's cellular proteins. HIV-1 protease is of particular interest because it is responsible for the proteolytic processing of the gag and gag-pol proteins to form infectious virions. See Kramer, *Science* 231:1580 (1986) and Kohl, *Proc. Natl. Acad. Sci.* 85:4686 (1988). The HIV protease recognizes and cleaves the octapeptide sequence SQNYPIVQ, (SEQ ID NO:1) corresponding to the Pr55 gag p17/p24 cleavage site, and the decapeptide sequence VSFNFPQITL, (SEQ ID NO:2) corresponding to the p6/PR cleavage site of the gag-pol protein. See Krausslich, *Proc. Nat. Acad. Sci.* 86:807–11 (1989). Thus, peptide sequences that are recognized and cleaved by such HIV proteases can be employed as the recognition site.

When it is desirable that the cross-linked enzyme donor polypeptide be cleaved proteolytically, a non-cleavable cross-linking agent may be used. This can be achieved by either total chemical peptide synthesis or by genetic fusion of the enzyme donor sequence with a sequence coding for the desired proteolytic cleavage recognition site. Preferably the proteolytic cleavage recognition site will be incorporated into the enzyme donor sequence internally, such that the protease cleavage site is positioned between the two reactive amino acid residues of the enzyme donor used for the cross-linking reaction. An inert, or non-cleavable, cross-linking moiety (for example bis-maleimidohexane) is then employed to produce the cross-linked enzyme donor-protease substrate chimera. The chimeric enzyme donors can be made employing recombinant DNA methodologies by genetic insertion of the gene encoding the desired recognition site into the gene encoding the enzyme donor sequence at a suitable endonuclease recognition site. Plasmid vectors containing β-galactosidase enzyme donor DNA sequences are well known in the art. Recombinant polymerase chain reaction cloning can be performed employing oligonucleotide primers containing the coding sequence of interest and suitable restriction enzyme cloning sites to construct mutant enzyme donors having an internal protease susceptible sequence. Alternatively, chemical synthesis of the enzyme donor polypeptide and a protease recognition site from amino acid starting material by sequential addition of amino acids or protected amino acids to a growing peptide chain can be employed. Such techniques are known to those skilled in the art. See, for example, U.S. Pat. No. 4,493,795 and the scientific literature cited therein.

The release of the cross-link, or opening of the cyclic peptide, may be achieved in several different fashions. If the desired analyte is a site-specific protease (for example HIV protease) the cross-linked enzyme donor polypeptide can include a sequence that contains a recognition site for that protease. The activity of the protease cleaves the enzyme donor at the protease recognition site, releasing the enzyme donor to complement with enzyme acceptor, thereby resulting in β-galactosidase activity, which is easily measured. See, for example, Baum, *Proc. Nat. Acad. Sci.* 87:10023–27 (1990) which discloses insertion of an HIV protease recognition site into a non-cross-linked β-galactosidase gene, and Liebig, *Proc. Nat. Acad. Sci.* 88:5979–83 (1991) which discloses fusion of a human rhinovirus proteinase with a non-cross-linked α-fragment of β-galactosidase. Another exemplary analyte is interleukin-1-β converting enzyme (ICE protease), which plays a role in apoptosis (cell death). This protease enzyme has a well-defined specificity for the sequence -X-Val-Y-Asp-Z- (SEQ ID NO:3). Cleavage of the sequence by ICE protease occurs after the Asp. The minimal and best peptide substrate sequence found heretodate to elicit action of the ICE protease enzyme appears to be Ac-Tyr-Val-Ala-Asp-NH-CH$_3$(SEQ ID NO:4). See Thornberry, *Nature* 356:768–74 (1992). A potent inhibitor of ICE protease contains the sequence Ac-Tyr-Val-Ala-Asp-*, (SEQ ID NO:5) where * stands for chloromethylketone. See *Nature* 375:78–81 (1995). Incorporation of the ICE protease recognition site into a synthetic cross-linked enzyme donor polypeptide would permit the development of a simple, rapid assay for this important protease.

If the desired analyte is a specific nucleotide sequence, i.e., a target nucleotide, the cross-linking agent can comprise a single-stranded oligonucleotide sequence complementary to the target nucleotide sequence. The presence of the analyte nucleotide sequence results in hybridization between the single-stranded oligonucleotide sequence and the target nucleotide sequence. This newly formed duplex can then be cleaved by the addition of a double-stranded specific nuclease (for example a restriction endonuclease or RNAase H), resulting in the linearization of all cross-linked enzyme donors that have formed duplexes with complementary analyte nucleic acid sequences and complementation with enzyme acceptor to produce β-galactosidase activity. Exemplary analytes include the nucleic acid sequences of infectious pathogens such as bacteria and viruses, including, for example, mycobacteria tuberculosis, streptococcus, N. gonorrhea, HIV, herpes viruses such as cytomegalovirus, Epstein Barr virus, varicella zoster virus and herpes simplex, hepatitis and chlamydia.

Several additional groups of analytes or chemical environmental conditions can also be detected or measured using this technology. For example, the cross-linking agent selected could be one that is sensitive to cleavage by a specific chemical or environmental condition (pH, temperature, oxidation, reduction, etc.). Enzymes which do not directly cleave the cross-linking agent but whose activity results in the production of a metastable linker which can subsequently undergo cleavage (indirect linker cleavage), are also detectable by this method. An example of this is a galactosyl- or phosphate-derivatized, acetal-containing, linker in which the activity of the enzymes β-galactosidase or phosphatase, respectively, result in a severely destabilized and ultimately cleaved cross-linker. In this embodiment, it should be noted that when the analyte is itself used as an enzyme label (for example β-galactosidase, alkaline phosphatase, peroxidase, etc.) the present invention is useful as a powerful signal amplification system, because upon cleavage of the first substrate, i.e., the cross-linked enzyme donor containing enzyme cleavable cross-linker, an active enzyme is formed that can cleave multiple molecules of a second colorimetric, fluorescent or chemiluminescent substrate. Such cross-linkers have the formula W—(CH$_2$)$_n$—X—CH(OY)—(CH$_2$)$_n$—Z wherein W and Z are each a functional group selected from the group consisting of maleimide, succinimide and thiocyanate; n is a number from 1 to 10; X is oxygen, sulfur or nitrogen; and Y is an enzymatically cleavable moiety selected from the group consisting of galactose, mannose, glucose, phosphate, butyrate and acetate.

As described above, in an embodiment where the analyte is an enzyme, for example HIV-1 protease or N. gonorrhea protease, the cross-linking agent may comprise a chemical moiety that acts as a substrate site for the analyte enzyme. The enzyme reacts with the substrate site to destabilize the cross-linking agent, causing it to spontaneously hydrolyze to yield linearized enzyme donor. For example, acetal glycosides of aldehydes are known that, upon cleavage by a specific glycosidase enzyme, produce hydroxyacetals which spontaneously hydrolyze in aqueous solution to yield parent aldehydes. Based on this knowledge, a novel homobifunctional cross-linking agent was designed that contains a glycosyl acetal moiety. Upon removal of the glycosyl residue by the action of the glycosidase enzyme, the hydroxy acetal is generated which spontaneously hydrolyses. The net result is cleavage within the cross-linking agent and consequent linearization of the cross-linked enzyme donor polypeptide. These glycosyl-containing cross-linking agents have the formula

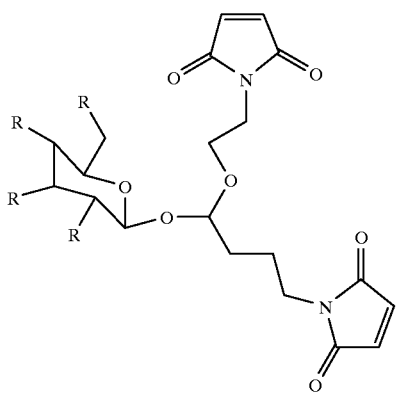

wherein R is hydroxy or acetate.

Additionally, it is possible to construct cross-linking agents which are susceptible to cleavage by chemical or environmental conditions. For example, it is possible to select or design cross-linking agents having spacers between the cross-linking moieties which are cleaved by acid, base, oxidation, reduction, temperature, light and so forth. An exemplary cross-linking agent useful for this purpose is the acid-labile 2,2-bis-maleimidoethoxypropane (BMEP), which is cleaved by mild acid hydrolysis. Other such reagents are known in the art and may be employed in an analogous manner.

The enzyme donor polypeptide to be cross-linked may comprise, for example, an N-terminal sequence of β-galactosidase. β-galactosidase enzyme donor sequences are known in the art. See U.S. Pat. No. 4,708,929; Langley and Zabin, *Biochemistry* 15:4866 (1976); Zabin, *Mol. and Cellular Biochem.* 49:84 (1982); Henderson, *Clin. Chemistry* 32:1637 (1986); Khanna, *Amer. Clin. Lab.* 8:14 (1989) and Coty, *J. Clin. Immunoassay* 17:144 (1994).

The cross-linked enzyme donor polypeptides of this invention make it possible to design and construct assays having little or no background interference due to undesired spontaneous enzyme complementation.

Other aspects of the present invention include methods for making the cross-linked enzyme donor polypeptides and assay methods which employ the cross-linked enzyme donor polypeptides of the present invention.

The method of making the cross-linked enzyme donor polypeptides of the invention comprises reacting a β-galactosidase enzyme donor in a mixture with a cross-linking agent under reaction conditions suitable to cause the cross-linking agent to covalently attach to two reactive amino acid residues of the enzyme donor and isolating the cross-linked peptide from the reaction mixture.

The assay method of the invention is usually conducted in an assay medium comprising the desired reagents in a suitable buffer. The buffer formulation is generally not critical but must allow interaction between the analyte of interest and the intramolecularly cross-linked enzyme donor in such a way as to effect linearization of the enzyme donor in the presence of the analyte. In general, any buffer compatible with complementation of β-galactosidase fragments is acceptable including phosphate buffer, MOPS buffer and the like. In one embodiment of the invention, the buffer has a concentration of about 100 mM to about 300 mM sodium phosphate, about 100 mM to about 500 mM sodium chloride, about 1 mM to about 6 mM magnesium chloride, about 5 mM to about 15 mM EGTA (ethylene glycol tetraacetic acid ) or EDTA (ethylenediamine tetraacetic acid ) and about 5 mM to about 200 mM sodium azide having a pH of about 6 to about 8.

A chelating agent can be added to any polypeptide or protein containing cysteine or methionine residues to protect against metal catalyzed oxidation. Addition of a stabilizing amount of chelating agent for metal ions (such as EDTA or EGTA) is desirable. A bactericide, such as sodium azide, can be present to prevent bacterial growth, especially during storage.

Other materials can be present including but not limited to magnesium ions or other ions for enzyme activity, reagents to prevent degradation of cysteine residues such as dithiothreitol (DTT), solubilizing agents such as ethylene glycol, and nonionic surfactants such as fatty acid condensation products of sorbitol and ethylene oxide, e.g., TWEEN 20 (® ICI Americas, Inc.), and the like. Methionine and bovine serum albumin (BSA) can also be present.

The storage stable assay medium is typically aqueous. The enzyme donor polypeptide is usually present at a concentration from about 2 pM to about 5 mM and enzyme acceptor is present in varying degrees of molar excess.

The sample can be obtained from any source of interest, organic or inorganic. The sample will generally be a liquid but can also be an extract of a solid material. The amount of the sample that can be used in conjunction with the present invention depends, among other things, upon the concentration of the analyte, the nature of the sample, and the sensitivity of the assay.

After combining the various reagents of the assay medium, the sample, and the appropriately cross-linked enzyme donor polypeptide to form a reaction mixture, the medium will usually be incubated for at least 0.2 minutes and usually not more than about 30 minutes, preferably from about 1 minute to about 10 minutes. The temperature and duration of the incubation will be compatible with the ability of the analyte or chemical condition of interest to exert its ability to result in the cleavage of the appropriate cross-linked enzyme donor if the analyte is present. In some formats, additional assay components and incubations may be necessary. Enzyme acceptor polypeptide and β-galactosidase substrates are then added together or separately and complementation activity is measured.

An enzyme substrate is used in the method of the invention that, when cleaved by β-galactosidase, results in a detectable change in the amount of light absorbance (optical density) or emission. That is, cleavage of the substrate results in the appearance or disappearance of a colored, chemiluminescent or fluorescent product suitable for spectrophotometric, chemical or fluorometric analysis. Substrates suitable for use with β-galactosidase include but are not limited to p-aminophenyl-β-D-galactopyranoside, 2'-N-(hexadecanol)-N-(amino-4'-nitrophenyl)-β-D-galactopyranoside, 4-methylumbelliferyl-β-D-galactopyranoside, naphthyl-A-S-B1-β-D-galactopyranoside, 2-naphthyl-A-S-B1-β-D-galactopyranoside monohydrate, o-naphthyl-β-D-galactopyranoside, p-naphthyl-β-D-galactopyranoside, phenyl-β-D-galactopyranoside, 5-bromo-4-chloro-3-indolyl-β-D-galactopyranoside, resorufin-β-D-galactopyranoside, 7-hydroxy-4-trifluoromethylcoumarin, ω-nitrostyryl-β-D-galactopyranoside, fluorescein-β-D-galactopyranoside, chlorophenol red β-galactoside and the like. Preferred substrates are chlorophenol red β-galactoside (CPRG) and o-nitrophenyl-β-D-galactoside (ONPG). Incubation with the enzyme substrate results in the cleavage of the substrate to produce a product that is detectable, preferably by color.

Unless specified otherwise above, the relative amounts of reagents used in the invention can vary widely to provide for concentrations of the reagents which can substantially optimize the sensitivity of the assay method. The reagents can be provided as dry powders, usually lyophilized, including any excipients, which on dissolution will provide for a reagent solution having the appropriate concentration for performing the assay method of the invention.

EXAMPLE 1

Intramolecular cross-linking of ED28 via native cysteine residues

ED28 is an enzyme donor polypeptide comprising 90 amino acids and containing two cysteine residues at amino acid positions 23 and 68. Positions 23 through 73 comprise the N-terminus of native β-galactosidase (using the convention of numbering the N-terminal Met residue "1"). The sequence of ED28 is also disclosed in U.S. Pat. No. 4,708,929, which describes how to make it. It was intramolecularly linked by forming a disulfide bond between the two cysteine residues at amino acid positions 23 and 68.

ED28, 2.5 mg, was dissolved in 50 mM sodium phosphate buffer, pH 8.5, containing 30% acetonitrile (0.5 ml). The solution was applied to a prepacked SEPHADEX G25 high molecular weight purification column (NAP5, ® Pharmacia, Inc.) which had been previously equilibrated with 5 column volumes of 30 mM sodium phosphate, pH 8.5, containing 39% acetonitrile. The ED28 was eluted with 1 ml of the same buffer. This procedure ensured removal of any low molecular weight reducing agents, such as dithiothreitol, which would prevent disulfide bond formation. The resultant solution was incubated with stirring for 12 hours, after which time the ED28 was about 95% converted to a disulfide-bonded molecule.

The cross-linked ED was purified by reverse-phase HPLC on a C4 RPLC column (Vydac Protein C4, 25 cm×10 mm). The column was developed at a flow rate of 4 ml/minute. A 23 to 33% gradient was established over a 45 minute time period using concentrations beginning with weak eluent of 0.1% trifluoroacetic acid (TFA) in $H_2O$ and ending with strong eluent of 0.1% TFA in acetonitrile. A sample of the purified, intramolecularly cross-linked material was treated with a 10 mM solution of the reducing agent DTT and reinjected onto the HPLC. As expected, the elution profile corresponded to the linearized material.

To confirm inhibition of the complementation activity of the cysteine-linked ED28 polypeptide, a CEDIA assay (® Microgenics Corp., Concord, Calif.) was performed using this material in the presence and in the absence of DTT. Solutions of cross-linked and linear ED28 (20 pmols) were prepared and incubated with enzyme acceptor EA22 (20 U/test), which comprises the complementing β-galactosidase fragment with a deletion of the amino acids from positions 13 to 40, and CPRG (2 mg/ml) in a buffered solution (dipotassium hydrogen phosphate, 210 mM; potassium dihydrogen phosphate, 150 mM; sodium chloride, 400 mM; EGTA, 10 mM; magnesium acetate, 2 mM; methionine, 10 mM; TWEEN 20, 0.05%; PLURONIC 101 (® BASF Corporation), 0.001%; Dextran T40, 4%; bovine serum albumin, 0.1%; sodium azide, 10 mM; pH 6.95) at 37° C. for 4 minutes. The rate in absorbance at 574 nm was measured per minute between 4 and 6 minutes. The results are shown in Table I below.

TABLE I

| Enzyme Donor | Reducing Agent | mAU/min @ 574 nm |
| --- | --- | --- |
| Cross-linked ED28 | None | 42 |
| Cross-linked ED28 | DTT | 344.5 |
| Linear ED28 | None | 346 |
| Linear ED28 | DTT | 345.2 |

These results demonstrate that the complementation activity of the cysteine-linked ED28 polypeptide was 12% of the ED28 which had been linearized by chemical reduction with DTT. The presence or absence of DTT had no effect on fresh, reconstituted linear ED28.

EXAMPLE 2

Intramolecular cross-linking of ED28 with a homobifunctional acid-labile cross-linking moiety The acid-labile, homobifunctional cross-linking agent 2,2 bis-maleimidoethoxypropane (BMEP), which can be made following the method of Srinivasvachar, *Biochemistry* 28:2501 (1989), was used to cross-link ED28. This cross-linking agent contains two maleimide groups, which react rapidly and specifically with sulfhydryl groups to form stable covalent bonds. The linkage between the two maleimide groups contains a ketal moiety that renders the cross-linker acid-labile. This cross-linking agent was used to form an intramolecular cross-link between the two cysteine residues of ED28.

ED28, 1.0 mg, was dissolved in 50 mM sodium phosphate buffer, pH 7.0, containing 39% acetonitrile (0.5 ml) to remove any low molecular weight reducing agents such as DTT which would prevent cross-linking. The solution was applied to a prepacked SEPHADEX G25 column previously equilibrated with 5 column volumes of 30 mM sodium phosphate, pH 7.5, containing 30% acetonitrile. The ED28 was eluted with 1 ml of the same buffer. To the eluent was added 11×0.1 equivalent aliquots of BMEP in acetonitrile (5 μl total volume) over a 30 minute time period. The reaction mixture was then incubated for 1 hour at room temperature, after which time the starting material was completely converted to cross-linked product.

The BMEP cross-linked ED28 was purified by reverse-phase HPLC on a C4 RPLC column. The column was developed at a flow rate of 4 ml/minute. Using a strong eluent isochratic profile of 24.5%, the purified material was eluted using concentrations of weak eluent of 100 mM triethylammonium acetate (TEAA) in $H_2O$ and strong eluent of acetonitrile. The purified material was lyophilized and stored at −80° C. A sample of the purified material was reconstituted in water and the pH adjusted to 2.0 with 0.1 M HCl and incubated for 3 minutes at room temperature. The pH was then adjusted to 6.8 employing a buffered solution (see Example 1) and the complementation activity with enzyme acceptor protein determined as described in Example 1. The results are shown in Table II below.

TABLE II

| Enzyme Donor | Treatment | mAU/min @ 574 nm |
| --- | --- | --- |
| Cross-linked ED28 | None | 22.5 |
| Cross-linked ED28 | pH 2.0 for 3 min | 925 |

TABLE II-continued

| Enzyme Donor | Treatment | mAU/min @ 574 nm |
|---|---|---|
| Linear ED28 | None | 930 |
| Linear ED28 | pH 2.0 for 3 min | 927 |

These results demonstrate that the untreated BMEP-linked ED28 has 2.5% of the complementation activity of the acid treated BMEP-linked ED28. Thus, the cross-linked ED28 can be linearized by mild acid hydrolysis of the chemical cross-linking moiety. A control experiment employing linear ED28 demonstrates that the 3 minute acidic pretreatment had no effect on the complementation of linear ED28.

EXAMPLE 3

Intramolecular cross-linking of ED28 via a homobifunctional cross-linker and protease cleavage of the cross-linked ED28 with endoprotease Glu-C This example describes the construction and use of an enzyme donor polypeptide that is cross-linked using a moiety that is not cleavable under assay conditions. In this example, the recognition sequence for a protease analyte of interest is not incorporated into the cross-linker but rather into the amino acid sequence of the enzyme donor or attached to its N- or C-terminus. This can be accomplished by recombinant DNA techniques or by solid phase peptide synthesis techniques, both of which are well known to those of skill in the art. The action of the protease cleaves the cross-linked enzyme donor at the protease recognition site, thereby linearizing the intramolecularly cross-linked peptide and enabling its complementation with enzyme acceptor.

Demonstrating this concept, ED28 was cross-linked with the homobifunctional cross-linking agent bis-maleimidohexane. Use of this reagent results in the irreversible cross-linking of sulfhydryl moieties under mild conditions. See Partis, *J. Prot. Chem.* 2:263-77 (1983). ED28, 1.0 mg, was dissolved in 50 mM sodium phosphate buffer, pH 7.0, containing 30% acetonitrile (0.5 ml). The solution was applied to a prepacked SEPHADEX G25 previously equilibrated with 5 column volumes of 30 mM sodium phosphate, pH 7.0, containing 30% acetonitrile. The ED28 was eluted with 1 ml of the same buffer. To the eluent was added 11 ×0.1 equivalent aliquots of BMH in acetonitrile (5 µl total volume) over a 30 minute time period. The reaction mixture was then incubated for 2 hours at room temperature, after which time the starting material was completely converted to cross-linked product.

The BMH cross-linked ED28 was purified by reverse-phase HPLC on a C4 RPLC column. The column was developed at a flow rate of 4 ml/minute. Using a strong eluent isochratic profile of 28.5%, the purified material was eluted using concentrations of weak eluent of 0.1% trifluoroacetic acid (TFA) in $H_2O$ and strong eluent of 0.1% TFA in acetonitrile. The purified material was lyophilized and reconstituted in 25 mM ammonium carbonate buffer, pH 7.8. The buffered sample was then incubated with 10 µg endoproteinase Glu-C protease (from *S. aureus* V8, Boehringer Mannheim) for 1 hour at room temperature. Enzyme acceptor protein (50 µl, 500 U/ml) and CPRG solution (50 µl, 3 mg/ml) were added, the plate was incubated at 37° C. and the absorbance at 570 nm was measured. The results are shown in Table III below.

TABLE III

| Sample | mAU/min @ 570 nm |
|---|---|
| Without protease treatment | 25 |
| With protease treatment | 713 |

This Glu-C protease specifically cleaves peptides at the C-terminal side of glutamic acid residues. Hence, the specificity of this protease for glutamic acid residues 62 and 63 of ED28 was exploited to linearize the BMH cross-linked ED28 at those positions rather than via the BMH moiety. Upon treatment of the cross-linked enzyme donor polypeptide with Glu-C protease, activity was increased dramatically, about 24-fold, indicating that cleavage had occurred.

EXAMPLE 4

Preparation of homobifunctional bis-maleimidoacetal cross-linking agent

Synthesis of N-(2-trimethylsiloxyethyl)-maleimide

As shown in FIG. 1, to a solution of ethanolamine (1.8 g, 29.5 mmol) in saturated sodium bicarbonate solution (100 ml) was added N-methoxycarbonylmaleimide (95 g, 32.3 mmol) in portions with vigorous stirring at 0° C. The mixture was allowed to warm to room temperature and stirred for 1 hour. The pH of the mixture was adjusted to 6–7 by careful addition of concentrated sulfuric acid (5 ml). The resultant solution was freeze dried and the solid residue extracted with ethyl acetate (2×400 ml) by stirring for 30 min. with each extraction. The ethyl acetate extracts were collected by filtration and evaporated in vacuo to afford N-(2hydroxyethyl)maleimide (formula I) as a white solid (4.0 g, 96% yield); thin layer chromatography (TLC), Rf=0.27, ethyl acetate/petroleum ether 1:1.

To a solution of N-(2-hydroxyethyl)maleimide (0.2 g, 1.41 mmol) in dry dichloromethane (10 ml) and triethylamine (0.22 ml, 1.57 mmol) at 0° C. was added chlorotrimethylsilane (TMS-Cl, 0.2 ml, 1.57 mmol). After stirring for 1 hour at room temperature, TLC analysis (ethyl acetate/petroleum ether 1:1) indicated one spot (Rf=0.67). Solvent was removed in vacuo and the residue was dissolved in dichloromethane and filtered through a small silica gel column eluting with dichloromethane. The fractions containing product were pooled and evaporated in vacuo to afford N-(2-trimethylsiloxyethyl)-maleimide (formula II) as colorless flakes (0.3 g; 100% yield).

Synthesis of 4-maleimidobutyraldehyde

Figure 2:
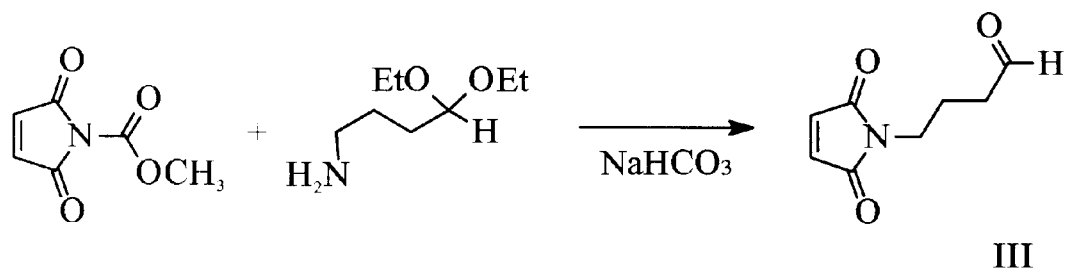
FIG. 2 illustrates a particular synthetic scheme for preparing 4-maleimidobutyraldehyde.

As shown in FIG. 2, to a solution of 4-aminobutyraldehyde diethylacetal (5 g, 31 mmol) in 100 ml of saturated bicarbonate was added N-methoxycarbonylmaleimide (4.91 g, 31.6 mmol) at 0° C. (icebath). After 15 minutes, tetrahydrofuran (100 ml) was added at room temperature and the resultant mixture stirred for 1 hour. The resultant mixture was then acidified with 1 N hydrochloric acid to pH 6–7 and extracted with ethyl acetate (3×200 ml). The combined organic extracts were dried ($MgSO_4$) and evaporated in vacuo. The crude product was purified by chromatography on silica gel 60 eluting with ethyl acetate/petroleum ether 1:2 to yield 4-maleimidobutyraldehyde diethylacetal as a yellow oil (4.31 g; 58%), TLC Rf=0.65, ethyl acetate/hexane 1:1.

4-Maleimidobutyraldehyde diethylacetal (2 g, 8.29 mmol) in tetrahydrofuran (20 ml) and water (0.5 ml) was stirred under argon and DOWEX 50X8 ion exchange resin ($H^+$, 2 g, ® Dow Chemical Co.) was added. After 12 hours stirring at room temperature, the solvent was decanted, dried (MgSO$_4$) and evaporated in vacuo to afford 4-maleimidobutyraldehyde (formula III) as a yellow oil which rapidly solidified on standing (1.38 g, 99%); TLC Rf=0.4, ethyl acetate/hexane 1:1. The 4-maleimidobutyraldehyde turned out to be extremely unstable, so that it was necessary to do all work-up at low temperatures (0° C.) and under complete exclusion of oxygen (inert atmosphere).

Figure 3:
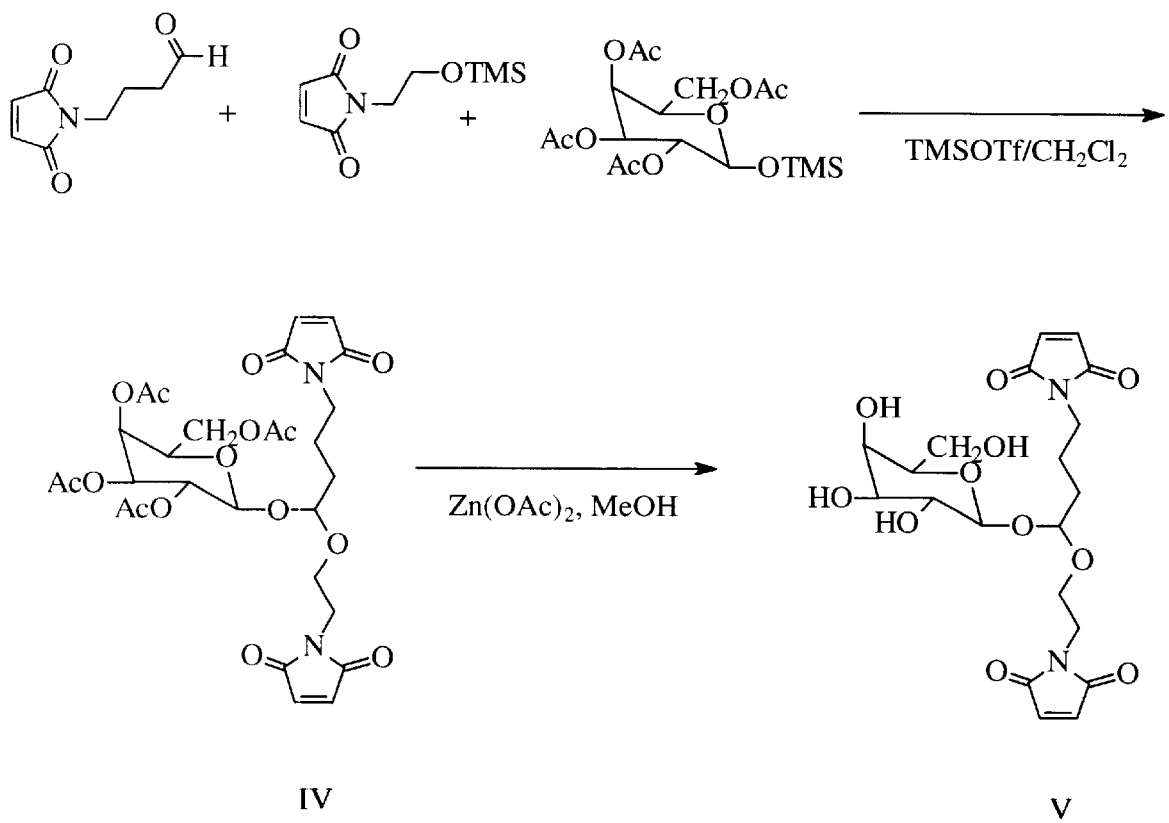
FIG. 3 illustrates a particular synthetic scheme for preparing 1,7-bismaleimido-4-O-(tetraacetyl-β-D-galactopyranosyl)-5-oxaheptane and 1,7-bis-(3'-methoxysuccinimido)-4-O-(β-galactopyranosyl)-5-oxaheptane.

Synthesis of 1,7-bismaleimido-4-O-(tetraacetyl-β-D-galactopyranosyl)-5-oxaheptane As shown in FIG. 3, to a stirred solution of 4-maleimidobutyraldehyde (1.82 g, 11 mmol), N-(2-trimethylsiloxyethyl)-maleimide (0.79 g, 3.5 mmol), 1-trimethylsilyloxy-2,3,4,6-tetra-O-acetyl-β-D-galactopyranose (1.52 g, 3.5 mmol) and molecular sieve [4 Å] in 40 ml dry dichloromethane was added TMSOTf (trimethylsilyl triflate, 0.67 ml, 3.5 mmol) at −78° C. under rigorous dry conditions and inert atmosphere (argon). The reaction mixture was quenched by addition of 1.5 ml triethylamine/methanol (1:1) after two days. The solvent was removed in vacuo after CELITE (® Celite Corp.) filtration (5 g). The crude product was chromatographed (ethylacetate/light petroleum, 1:1) to give 1,7-bismaleimido-4-O-(tetraacetyl-β-D-galactopyranosyl)-5-oxaheptane (formula IV) (1.78 g, 2.7 mmol) in 77% yield.

Deprotection of 1,7-bismaleimido-4-O-(tetraacetyl-β-D-galactopyranosyl)-5-oxaheptane To a stirred solution of 1,7-bismaleimido-4-O-(tetraacetyl-β-D-galactopyranosyl)-5oxaheptane (200 mg, 0.3 mmol) in 20 ml dry methanol was added Zn(OAc)$_2$ (60 mg, 0.3 mmol). The solution was refluxed for 9 hours under rigorous dry conditions. Tert-butylmethylether (20 ml) was added at room temperature. CELITE filtration (5 g) with 200 ml tert-butylmethylether/methanol (1:1), evaporation of solvent in vacuo, followed by chromatography (ethylacetate/methanol/triethylamine, 4:1:1) gave a mixture of 1,7-bismaleimido-4-O-(β-D-galactopyranosyl)-5-oxaheptane (formula IV) and 1,7-bis-(3'-methoxysuccinimido)-4-O-(β-D-galactopyranosyl)-5-oxaheptane (formula V) in a ratio of 1:2 (145 mg, 0.29 mmol) in 99% yield. Zn(OAc)$_2$ was dried at 80° C. (p=0.001 Torr) for 24 hours.

The 1,7-bismaleimido-4-O-(tetraacetyl-β-D-galactopyranosyl)-5-oxaheptane was used to prepare cyclic fusion peptides comprised of β-galactosidase enzyme donor and HIV gag sequences, constructed as set forth in Example 5 below.

EXAMPLE 5

Preparation of double Cys- HIV peptide-containing enzyme donors

Double cysteine-containing enzyme donor polypeptides which also contained an HIV protease recognition site were prepared by recombinant DNA techniques and by solid phase peptide synthesis.

*E. Coli* strain AMA 1004 (Casadaban, *Methods in Enzymology* 100:293, 1983) was used for expression of EA, ED, and complemented β-galactosidase. *E. coli* strain MC 1061 (Meissner, *Proc Nat Acad Sci* 84:4171, 1987) was used for isolation of recombinant clones.

Oligonucleotide primers were designed to amplify the β-galactosidase alpha region known as ED7 from the plasmid p187 with the addition of either the 8 residue (p17/p24) or 10 residue (p6/PR) HIV protease recognition sites carrying a HindIII restriction site for clone selection. The N-terminal primer for amplification of the ED7-HIV p17/p24 gene (5'-GATACGAATTCTCAGAACTATCCG-ATCGTTCAGTCACTGGCCGTCGTTTTACAA-3') (SEQ ID NO:6) contained the 8 residue HIV protease recognition site.

The N-terminal primer for amplification of the ED7-HIV p6/PR gene (5'GATACGAATTCTGTAAGCTTTAAC-TTTCCGCAGATCACCCTGCTGGCCGTCGTTTTA CAA-3') (SEQ ID NO:7) contained the 10 residue HIV protease recognition site. Both amplifications used the C-terminal primer KM1 (5'-CTGGCTTAACTATGCGGCATC-3') (SEQ ID NO:8). PCR amplifications were run in an MJ Research minicycler PTC-150 beginning with denaturation at 94° C. for 1 minute followed by 40 cycles of 92° C. for 40 seconds, 65° C.for 40 seconds, and 75° C. for 1.5 minutes and a final elongation step of 75° C. for 5 minutes. Reactions were 100 μl volumes and run as hot starts using PCR Gems (Perkin/Elmer).

Amplified DNA was cleaned by phenol-chloroform extractions and precipitated in ethanol. Resuspended material was trimmed by EcoR1 and Sal1 digestion and purified by agarose gel electrophoresis. Gel purified insert DNA was ligated into p187 EcoR1/Sal vector. The resulting clone carried the ED7 gene with either the HIV p17/p24 or p6/PR cleavage site as an internal gene fusion cassette inserted at an EcoR1 site located near the 3' end of the ED7 gene. The correct clone was identified by the presence of the HindIII site located in the PCR product and verified by DNA sequencing. For expression and purification, the ED7-HIV genes were transferred by BamH1/Sal1 digestion into a BamH1/Sal1 vector (p43) carrying the large fragment of β-galactosidase, EA46, which complements in vivo with the ED7-HIV gene products.

ED7-HIV p17/24, ED7-HIV p6/PR and EA46 proteins were induced at 40° C. from the lambda PL promotor through inactivation of the plasmid CI857 repressor. The cells were harvested after 4 hours of induction, and the complemented β-galactosidase was purified by a 40% ammonium sulfate precipitation followed by ion exchange chromatography on Q-SEPHAROSE. The complemented enzyme was denatured in 10 M urea, and the recombinant ED-HIV proteins were separated from denatured EA46 by size exclusion chromatography in 6 M urea. Fractions containing the ED-HIV proteins were concentrated with an Amicon stir cell and dialyzed into a neutral TRIS buffer. Any residual contaminating proteins were removed through ion exchange chromatography on Q-SEPHAROSE.

The target peptides were also synthesized on an Applied Biosystems (ABI) Model 431 A solid phase peptide synthesizer, using Fmoc protected amino acids activated with 2-1H-benzotriazol-1-yl)-1,1,3,3-tetramethyluronium hexafluorophosphate (HBTU; ABI user bulletin #33). The synthesis was carried out at 0.25 mmol scale, and a pre-loaded HMP resin was used as the solid phase. The deprotection and coupling times were extended from the standard times recommended by the manufacturer. The following amino acids were used: Fmoc-Ala, Fmoc-Arg (PVC), Fmoc-Asn (Trt), Fmoc-Asp (OtBu), Fmoc-Cys (Trt), Fmoc-Gln (Trt), Fmoc-Glu (OtBu), Fmoc-Gly, Fmoc-His (Trt), Fmoc-Leu, Fmoc-Lys (Boc), Fmoc-Phe, Fmoc-Pro, and Fmoc-Ser (tBu). The N-terminus was not acetylated and the C-terminus was left as the carboxy form.

Cleavage of the crude peptide-resin was accomplished by incubation for 3 hours in a solution of TFA containing the carbonium scavengers, water (4%), thioanisole (4%), phenol (1.5%), and 1,2-ethane dithiol (2%). The mixture was filtered, evaporated to an oil and precipitated with cold diethyl ether. Purification of the crude peptide was done by reverse-phase HPLC, using a Vydac 2.2×300 mm C18 column and a 16–41% acetonitrile/water gradient, with 0.1% TFA as the counter-ion. The purified peptide was designated SED35 and contained the VSFNFPQITL (SEQ ID NO:2) protease cleavage site.

EXAMPLE 6

Cross-linking ED7-HIV fusion peptide with 1,7-bismaleimido-4-O-(tetraacetyl-β-D-galactopyranosyl)-5-oxaheptane The ED7-HIV fusion peptide from Example 5 was then cross-linked by the covalent linkage of 1,7-bismaleimido-4-O-(tetraacetyl-β-D-galactopyranosyl)-5-oxaheptane between residues 10 and 53 of the fusion peptide.

The ED7-HIV fusion peptide ED7-HIV p17/p24 was reconstituted in 50 mM sodium phosphate buffer, pH 7.0(1 ml), and the solution was applied to a prepacked SEPHADEX G25 column. The fusion peptide was eluted with the same buffer (1.5 ml). To the eluent containing 362 μg/ml of the fusion peptide (97% recovery) was added 11×0.1 equivalent aliquots of 1,7-bismaleimido-4-O-(tetraacetyl-β-D-galactopyranosyl)-5-oxaheptane in acetonitrile (5 μl total volume; 38 μg total) over a 30 minute time period. The reaction mixture was then incubated for 30 minutes at room temperature.

The cross-linked ED-HIV fusion peptide was purified by HPLC employing a Vydac Protein C4 (25 cm×10 mm) semi-preparative HPLC column using 100 mM TEAA, pH 6.5 as solvent A and acetonitrile as solvent B. The column was developed at a flow rate of 4 ml/minute. A 22 to 40% gradient of solvent B was established over a 15 minute time period. Linear ED-HIV fusion peptide exhibited a retention time of 13 minutes. Cross-linked ED-HIV fusion peptide exhibited a retention time of 14.2 minutes. Fractions containing the product were pooled and lyophilized. The yield of cross-linked ED-HIV fusion peptide was 155 micrograms.

To test for complementation activity, samples of the linear ED-HIV fusion peptide and the cross-linked ED-HIV fusion peptide were reconstituted in assay buffer and serially diluted across a microtiter plate. Enzyme acceptor (2050 U/ml) and CPRG (1 mg/ml), 50 μl each, were added to each well and the change in absorbance at 570 nm monitored every 30 seconds in a V max plate reader. The results are shown in Table IV below:

TABLE IV

| Enzyme Donor | Concentration | mAU/min @ 570 nm |
|---|---|---|
| Linear ED-HIV fusion peptide | 1.84 pmols | 57.25 |
| Cyclic ED-HIV fusion peptide | 1.84 pmols | 1.29 |
| Linear ED-HIV fusion peptide | 3.68 pmols | 85.18 |
| Cyclic ED-HIV fusion peptide | 3.68 pmols | 2.17 |

These results demonstrate that the complementation activity of the cross-linked enzyme donor was 2.5% that of the linear enzyme donor. A second HPLC purification was carried out using the once-purified material and the repurified cyclic ED-HIV fusion peptide tested again in this assay. In this test, the cyclic ED-HIV fusion peptide exhibited only 0.04% of the complementation activity exhibited by the linear ED-HIV fusion peptide, indicating that the higher activity seen after only one HPLC purification is likely due to the presence of linear ED-HIV contaminant.

EXAMPLE 7

Cross-linking SED35-HIV fusion peptide with 1,7-bismaleimido-4-O-(tetraacetyl-β-D-galactopyranosyl)-5-oxaheptane SED35 is a 60 residue fusion peptide produced by solid phase peptide synthesis that contains a 14 residue N-terminal sequence composed of the decapeptide VSFNFPQITL (SEQ ID NO:2) corresponding to the p6/PR HIV-1 protease cleavage site and amino terminal residues GGGC (SEQ ID NO:9) in the HIV gag/pol polypeptide and a 46 residue C-terminal sequence composed of residues 28 through 73 of ED28.

SED35, (0.5 mg, 75 nmols) in 100 mM phosphate buffer, pH 6.5, containing 5 mM EDTA and 30% acetonitrile was combined with 5 μl aliquots of 6×0.2 mol equivalents of 1,7bismaleimido-4-O-(tetraacetyl-β-D-galactopyranosyl)-5-oxaheptane in acetonitrile (57 μg total) over a 30 minute period of time. The reaction mixture was then allowed to incubate 30 minutes at room temperature.

The cross-linked ED-HIV fusion peptide was purified by HPLC employing a Vydac Protein C4 (25 cm×10 mm) semi-preparative HPLC column using 100 mM TEAA, pH 6.5 as solvent A and acetonitrile as solvent B. The column was developed at a flow rate of 4 ml/minute. A 35 to 40% gradient of solvent B was established over a 20 minute time period. Fractions containing the cross-linked ED-HIV fusion peptide were pooled.

EXAMPLE 8

ELISA assay format for determining HIV-1 protease inhibitor

An ELISA plate format was used to determine $IC_{50}$ values (concentration of inhibitor that causes a 50% reduction in enzyme activity) of various inhibitors using a kinetic microtiter plate reader.

A stock solution of the cross-linked chimeric peptide SED35-HIV p6/PR containing HIV-1 substrate sequence VSFNFPQITL (SEQ ID NO:12) corresponding to the p6/PR cleavage site of the HIV gag/pol polypeptide was prepared at a concentration of 1 μg/ml in protease assay buffer (100 mM NaOAc, 1 M NaCl, 0.1% BSA, 1 mM EDTA, pH 5.0). Recombinant HIV protease was prepared at a concentration of 10 μg/ml, also in protease assay buffer. HIV protease inhibitors were dissolved in dimethyl sulfoxide (DMSO) and diluted to working concentrations in protease assay buffer containing 10% DMSO. β-galactosidase enzyme acceptor protein EA22 was prepared in β-galactosidase assay buffer to give a final concentration of 500 U/ml. CPRG was dissolved in β-galactosidase assay buffer at a concentration of 3 mg/ml.

HIV protease inhibitors 94-001, 94-002, 94-003, 94-004 and 94-005 were dissolved in DMSO to give stock concentrations of 394 nM, 78.8 nM and 15.76 nM. See Ghosh et. al., *J. Med. Chem.* 37:1177–88 (1994) and Ghosh et. al., *J. Med. Chem.* 37:2506–8 (1994). Recombinant HIV-1 protease (homodimer, Mr=22,000) stock solution (10 μl, 4.54 pmols), protease inhibitor stock solutions (10 μl), cyclic ED-HIV stock solution (25 μl, 3.57 pmols), EA22 solution (50 μl, 25 U) and CPRG solution (50 μl) were pipetted into the wells of a polystyrene microtiter plate. The plate was incubated for 5 min. at 37° C. and then the absorbance at 570 nm monitored for 20 min. The $IC_{50}$ value for each of the inhibitors was determined from graphs of Vmax vs time. (The $IC_{50}$ is proportional to the Ki value for the inhibitor).

The relative $IC_{50}$ values found for each of the inhibitors is given in Table V.

TABLE V

| Inhibitor | Relative $IC_{50}$ (nM) |
|---|---|
| 94-001 | 5 |
| 94-002 | 4 |
| 94-003 | 2.5 |
| 94-004 | 3 |
| 94-005 | 7.5 |

EXAMPLE 9

COBAS MIRA assay format for determining HIV-1 protease inhibitor

A three reagent assay system was used to determine $IC_{50}$ concentrations of various inhibitors. A COBAS MIRA analyzer (® Roche Diagnostic Systems, Inc., Nutley, N.J.) was used.

Sample (inhibitor 94-001, 94-002, 94-003 or 94-004) was diluted with an HIV protease buffer (10 mM sodium acetate, 1 M NaCl, 1 mM EDTA, 0.1% BSA, pH 5.0) modified with 10% DMSO to give final reagent inhibitor concentrations of 45.3 mM to 4.53 nM by dilution factors of ten.

Reagent 1 (R1) contained HIV protease diluted to a reagent concentration of 45 nM in HIV protease buffer.

Reagent 2 (R2) contained cross-linked enzyme donor SED35 at 0.30 mM and CPRG at 43 mg/ml in HIV protease buffer.

Reagent 3 (R3) contained EA22 diluted to a reagent concentration of 1315 U/ml.

The COBAS MIRA apparatus was programmed to deliver 10 µl of sample and 100 ml of R1 at time point one (T=0 minutes), 10 ml of R2 at time point two (T=2 minutes), and 95 ml of R3 at time point three (T=7 minutes). Rate values (absorbance changes within various time periods) were taken at time point four (T=9 to 11 minutes). These values were used to construct rate versus the log of inhibitor concentration graphs to determine $IC_{50}$ values. All assays were performed at 37° C. The data given in Table VI for inhibitor 94-001 is exemplary.

TABLE VI

| Inhibitor Concentration (M) | Rate (mAU/min) |
|---|---|
| $2.1 \times 10^{-7}$ | 849 |
| $2.1 \times 10^{-5}$ | 247 |
| $2.1 \times 10^{-3}$ | 90 |

Using the data, a rate versus log inhibitor concentration graph was constructed and a curve fitting program was applied to generate a logarithmic line equation, in this case $f(x)=-169*\ln(x)+602$, or $f(y)=-9.19*\ln(y)+60.9$. The midpoint of the rate data (50% response) was then determined and the value inserted into the $f(y)$ equation to generate the $IC_{50}$ concentration. Here, the midpoint value was 470 mAU/min and the $IC_{50}$ value was 4.35 nM. The results for the assay given in Table VII.

TABLE VII

| Inhibitor # | $IC_{50}$ (nM) |
|---|---|
| reference | 9.00 |
| 1 | 4.35 |
| 2 | 5.11 |
| 3 | 4.30 |
| 4 | 4.41 |

All publications and patent applications mentioned in this specification are herein incorporated by reference to the same extent as if each individual publication or patent application was specifically and individually indicated to be incorporated by reference. The invention now being fully described, it will be apparent to one of ordinary skill in the art that many changes and modifications can be made thereto without departing from the spirit or scope of the appended claims.

What is claimed is:

1. A cross-linking agent of the formula W—$(CH_2)_n$—X—CH(OY)—$(CH_2)_n$—Z wherein:

W and Z are each a functional group selected from the group consisting of maleimide, succinimide and thiocyanate;

n is a number from 1 to 10;

X is oxygen, sulfur or nitrogen; and

Y is an enzymatically cleavable moiety selected from the group consisting of glycosides, phosphate, butyrate and acetate.

2. The cross-linking agent of claim 1 wherein W and Z are maleimide and Y is galactose.

3. The cross-linking agent of claim 1, wherein the enzymatically cleavable moiety is a glycoside.

4. The cross-linking agent of claim 3, wherein the enzymatically cleavable moiety is an acetal glycoside.

5. The cross-linking agent of claim 3, wherein the enzymatically cleavable moiety is selected from the group consisting of galactose, mannose, and glucose.

6. A method for forming a cross-linked protein, comprising contacting the protein with the cross-linking agent of claim 3.

7. The cross-linking agent of claim 1, wherein the enzymatically cleavable moiety is selected from the group consisting of phosphate, butyrate and acetate.

8. A method for forming a cross-linked protein, comprising contacting the protein with the cross-linking agent of claim 1.

9. The method of claim 8, wherein the protein is a portion of an enzyme.

10. The method of claim 9, wherein the protein is an enzyme donor of β-galactosidase.

11. An enzyme portion cross-linked using the agent of claim 1.

12. A method of determining the presence or amount of an enzyme in a sample, comprising contacting any enzyme in the sample with an enzyme portion that has been cross-linked using the agent of claim 1, wherein the enzymatically cleavable moiety of the agent is cleavable by the enzyme to be determined.

13. A cross-linking agent of the formula

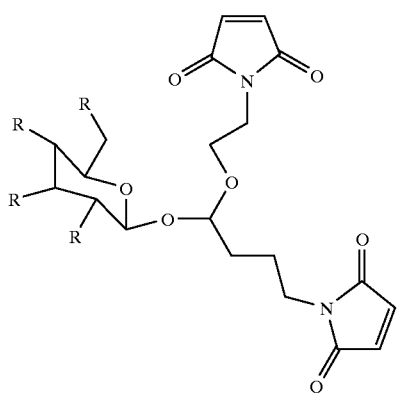

wherein R is hydroxy or acetate.

14. A method for forming a cross-linked protein, comprising contacting the protein with the cross-linking agent of claim 13.

15. An enzyme portion cross-linked using the agent of claim 13.

16. A method of determining the presence or amount of an enzyme in a sample, comprising contacting any enzyme in the sample with an enzyme portion that has been cross-linked using the agent of claim 13, wherein a moiety of the agent is cleavable by the enzyme to be determined.

17. The compound 1,7-bismaleimido-4-O-(tetraacetyl-β-D-galactopyranosyl)-5-oxaheptane.

18. The compound 1,7-bismaleimido-4-O-(β-D-galactopyranosyl)-5-oxaheptane.

* * * * *